United States Patent
Ho et al.

[11] Patent Number: 5,132,477
[45] Date of Patent: Jul. 21, 1992

[54] PROCESS FOR PRODUCING ALKYLAROMATIC LUBRICANT FLUIDS

[75] Inventors: Suzzy C. Ho, Plainsboro; Bruce P. Pelrine, Trenton; Margaret M. Wu, Belle Mead, all of N.J.

[73] Assignee: Mobil Oil Corporation, Fairfax, Va.

[21] Appl. No.: 693,161

[22] Filed: Apr. 29, 1991

[51] Int. Cl.$^5$ .............................................. C07C 2/66
[52] U.S. Cl. ...................................... 585/467; 585/11; 585/24; 585/26
[58] Field of Search ................. 585/11, 24, 26, 467

[56] References Cited

U.S. PATENT DOCUMENTS

| | | | |
|---|---|---|---|
| 3,442,964 | 5/1969 | Oldham | 585/467 |
| 4,368,342 | 1/1983 | Slaugh | 585/446 |
| 4,665,245 | 5/1987 | Quann | 585/316 |
| 4,827,064 | 5/1989 | Wu | 585/10 |
| 4,827,073 | 5/1989 | Wu | 585/530 |
| 4,914,254 | 4/1990 | Pelrine | 585/530 |

FOREIGN PATENT DOCUMENTS 3427319 1/1986 Fed. Rep. of Germany.

*Primary Examiner*—Asok Pal
*Attorney, Agent, or Firm*—Alexander J. McKillop; Charles J. Speciale; Malcolm D. Keen

[57] ABSTRACT

The thermal and oxidative stability of HVI-PAO olefin oligomers is improved by reaction of the oligomerization mixture containing the olefin oligomer, dimer and isomerized but unoligomerized olefin with an aromatic compound such as toluene, xylene or naphthalene. The reaction is carried out in the presence of an acidic catalyst, which may be heterogeneous solid catalyst such as an acidic clay or a crystalline zeolite such as MCM-22, a homogeneous Friedel-Crafts catalyst such as $AlCl_3$, $BF_3$ or their complexes or a supported catalyst such as $AlCl_3$ on graphite or silica. The reaction improves the yield and thermal stability of the lube range products. The olefinic oligomer mixture which is reacted with the aromatic compound is prepared from 1-alkene oligomerization in contact with a reduced metal oxide, preferably reduced chromium oxide, catalyst on support such as silica.

19 Claims, No Drawings

PROCESS FOR PRODUCING ALKYLAROMATIC LUBRICANT FLUIDS

CROSS REFERENCE TO RELATED APPLICATIONS

This application is related to the following applications:
Ser. No. 07/345,606, filed May 1, 1989, now U.S. Pat. No. 5,012,020,
Ser. No. 07/562,179, filed Aug. 3, 1990, now U.S. Pat. No. 5,015,795,
Ser. No. 07/629,946, filed Dec. 19, 1990,
Ser. No. 07/515,030, filed Apr. 26, 1990, now U.S. Pat. No. 5,019,670,
Ser. No. 07/344,935, filed Apr. 28, 1989,
Ser. No. 07/693,255, filed concurrently.

FIELD OF THE INVENTION

This invention relates to a process for producing alkylated aromatic compositions useful as lubricant basestock and lubricant additives. The invention also relates a process for producing lubricant compositions of high viscosity index (VI) and increased thermal stability by alkylating aromatics with high VI, low pour point poly-alpha-olefin oligomers.

BACKGROUND OF THE INVENTION

Efforts to improve upon the performance of natural mineral oil based lubricants by the synthesis of oligomeric hydrocarbon fluids have been the subject of important research and development in the petroleum industry for a large number of years and have led to the introduction of a number of superior polyalpha-olefin (PAO) synthetic lubricants produced by the oligomerization of alpha-olefins or 1-alkenes. In terms of lubricant property improvement, the thrust of the industrial research effort on synthetic lubricants has been toward fluids exhibiting useful viscosities over a wider range of temperature, i.e., improved viscosity index(VI), while also showing lubricity, thermal and oxidative stability and pour point equal to or better than mineral oil. These new synthetic lubricants exhibit lower friction characteristics and are therefore capable of increasing mechanical efficiency of various types of equipment including engines, transmissions, worm gears and traction drives, doing so over a wider range of operating conditions than mineral oil lubricants. Notwithstanding their generally superior properties, PAO lubricants are often formulated with additives to enhance those properties for specific applications. Among the more commonly used additives are oxidation inhibitors, rust inhibitors, metal passivators, antiwear agents, extreme pressure additives, pour point depressants, detergent-dispersants, viscosity index (VI) improvers, foam inhibitors and the like. This aspect of lubricant technology is described in Kirk-Othmer "Encyclopedia of Chemical Technology", 3rd Edition, Vol. 14, pp. 477-526, to which reference is made for a description of the use of such additives.

Improvements in synthetic lubricant technology have resulted both from new additive developments intended to address deficiencies in the lubricant (oligomer) basestocks as well as from developments in new base fluid (oligomer). Recently, lubricant compositions (referred to in this specification as HVI-PAO) of remarkable high VI coupled with low pour point have been developed. These lubricant compositions are described in U.S. Pat. Nos. 4,827,064 and 4,827,063, to which reference is made for a detailed description of these lubricants, methods for their preparation and of their properties and uses. These HVI-PAO materials comprise polyalpha-olefin oligomers prepared by the use of a reduced metal oxide, preferably reduced chromium, oligomerization catalyst. The lubricant product is characterized by a branch ratio less than 0.19, indicating a high degree of linearity and pour point below $-15°$ C. In its as-synthesized form, the HVI-PAO oligomer has olefinic unsaturation associated with the last of the recurring monomer units in the structure and this can be removed by a simple hydrogenative treatment to produce a stabilized, fully saturated oligomer product. Lubricants produced by the process cover the full range of lubricant viscosities and exhibit a remarkably high VI and low pour point even at high viscosity. Products of higher viscosity can also be produced by operating the oligomerization process at lower temperatures, typically $-20°$ to $+90°$ C., and these high viscosity products are useful as lubricant additives, especially VI improvers for both mineral and synthetic oils, as described in copending application Ser. No. 07/345,606, now U.S. Pat. No. 5,012,020, to which reference is made for a description of these higher viscosity oligomers, their properties and uses and of the method by which they may be made.

The process for preparing the HVI-PAO lubricants comprises, as noted above, contacting a $C_6$-$C_{20}$ 1-alkene feedstock with reduced valence state chromium oxide catalyst on porous silica support under oligomerizing conditions in an oligomerization zone to produce the high viscosity, high VI liquid hydrocarbon lubricant with branch ratios less than 0.19 and pour points below $-15°$ C. The oligomerization temperature is typically maintained at a value between 90° and 250° C. to produce the lubricant viscosity products. By operating the oligomerization process at lower temperatures, however, higher viscosity materials may be produced and these materials may be used as viscosity index (VI) improvers for lubricants, both of mineral oil and synthetic origin, as described Ser. No. 07/345,606. These higher viscosity HVI-PAO products typically have viscosities between 725 and 15,000 cS at 100° C., corresponding to weight molecular weights from about 15,000 to 200,000 and number molecular weights from about 5,000 to about 50,000; carbon numbers for these molecular weights are from about $C_{30}$ to about $C_{10,000}$, with a preferred range from about $C_{30}$ to about $C_{5,000}$. Like the liquid lubricant oligomers, these higher molecular weight oligomers are characterized by high VI coupled with excellent low temperature fluidity properties including pour point or the liquid products.

The lower molecular weight oligomers used for the production of low viscosity lubricants, for example, lubricants in the 5–10 cS range, are produced at relatively high temperatures which lead to the production of significant amounts of the non-lubricant range dimer a (about $C_{20}$ with decene as the starting olefin) as well by-products including isomerized olefin. Although the dimer may be reacted with the oligomer, as described in Ser. No. 07/562,179, filed Aug. 3, 1990, to improve the properties of the oligomer, the necessity of a separate fractionation and reaction steps renders this process somewhat less desirable than its potential would indicate.

The HVI-PAO oligomers have excellent fluid flow properties, as evidenced by their high VI values and low pour points but they do not necessarily posses the highest degree of thermal and oxidative stability under the most stringent conditions. For this reason, it would be desirable to improve their stability in these respects if this could be done without significant deterioration of their excellent rheological characteristics.

Alkylated aromatics, particularly alkylated naphthalene are known to possess good thermal and oxidative stability as disclosed in U.S. Pat. Nos. 4,211,665, 4,238,343, 4,604,491 and 4,714,7944 but these naphthalene derivatives do not usually possess good rheological properties: in particular, they have extremely poor VI, consonant with their aromatic character. In general, however, alkylated naphthalenes have been disappointing as lubricants although their good thermal and oxidative stability have made them suitable for use as transformer oils and heat exchange media. Efforts have therefore been made to combine the good thermal and oxidative stability of the aromatic materials with the excellent viscometric properties of the HVI-PAO oligomers by the introduction of aromatic moieties into the HVI-PAO molecules. Co-pending application Ser. No. 07/629,946, filed Dec. 19, 1990, describes a method of improving the thermal and oxidative stability of the HVI-PAO oligomers by alklating the unsaturated oligomer product with an aromatic compound such as benzene or naphthalene. The products have the enhanced stability and good solvency characteristics associated with the aromatic component while retaining the excellent rheological characteristics of the HVI-PAO oligomers. According to this method, the HVI-PAO oligomer is reacted with the aromatic compound in the presence of an alkylation catalyst such as a Lewis acid e.g. aluminum trichloride or born trifluoride or a solid acidic zeolite such as zeolite Y.

Co-pending application Ser. No. 07/515,030, filed Apr. 26, 1990, now U.S. Pat. No. 5,019,670, describes a method for improving the thermal and oxidative stability of HVI-PAO olefin oligomers by reaction with aromatic compounds such as naphthalene in the presence of the synthetic zeolite MCM-22. the products have enhanced stability while retaining the desirable viscometric characteristics of the original HVI-PAO staring material used as the alkylation agent in the reaction.

Co-pending application Ser. No. 07/344,935, filed Apr. 28, 1989, describes a method for improving the thermal and oxidative stability of HVI-PAO olefin oligomers by introducing aromatic moieties into the structure of the HVI-PAO by intramolecular cyclization and without the addition of extraneous sources of aromatic materials.

Although these methods are effective for the improvement of the thermal and oxidative stability of the HVI-PAO oligomers, the simultaneous improvement of yield and stability of the low viscosity oligomers still remains unsolved.

SUMMARY OF THE INVENTION

We have now found that the yield and stability—thermal and oxidative—of the HVI-PAO oligomers may be improved by treating the initial oligomerization mixture containing oligomer, dimer and unoligomerized olefin with an aromatic compound in the presence of an acidic catalyst.

The alkylated products have been found to possess good thermal and oxidative stability as well as good additive solvency characteristics in addition to their characteristically excellent fluid flow properties: the HVI-PAO hydrocarbons produced in this way retain the unique structurally-related features of the HVI-PAO olefinic oligomer and thereby exhibit an extraordinary combination of properties relating to high viscosity index and low pour point which makes them very useful as lubricant base stock. The lubricant products produced by the present process are also obtained in greater yields.

DETAILED DESCRIPTION

In the present process for producing the HVI-PAO products of improved thermal and oxidative stability aromatic hydrocarbons are produced in improved yields by reacting the oligomerization mixture, without preliminary fractionation or other separative treatment, with an aromatic compound in the presence of an acidic catalyst. The process is particularly applicable to the low viscosity HVI-PAO materials, for example, the 3-10 cS oligomers, which normally suffer a yield disadvantage resulting from the production of significant amounts of the olefin dimer at the same time as the oligomer. Thus, the present process permits the efficiency of the HVI-PAO production to be increased by the direct incorporation of the dimer fraction together with unreacted staring material or isomerized (but unoligomerized) starting material into the desired HVI-PAO product.

The oligomerization mixture form the initial oligomerization step contains, in addition to the lube-range oligomer (usually trimer and higher fractions), a significant fraction of the dimer as well as olefin which has not been dimerized or oligomerized but which has, nevertheless, undergone isomerization. The reaction of this intermediate product stream with the aromatic compound in the presence of the acidic catalyst results in a product which is believed to contain alkylated aromatics derived from the HVI-PAO oligomer as well as structures derived from the dimer and the isomerized olefin. The final lube range product is obtained in better yield, even in the low viscosity range (3-10 cS) and has improved stability.

OLEFIN OLIGOMER

The olefin oligomers are produced from the oligomerization of 1-alkenes over a reduced metal oxide catalyst, usually reduced chromium oxide on a silica support. As oligomerized, these HVI-PAO oligomers are mixtures of dialkyl vinylidenic and 1,2 dialkyl or trialkyl mono-olefin oligomers. Oligomerization of the olefin feed with the reduced metal oxide catalysts leads to an oligomer which is substantially free of double bond isomerization and has a high degree of linearity. Conventional PAO, on the other hand, formed by oligomerization over Lewis acid catalysts such as $BF_3$ or $ALCl_3$, are formed by a carbonium ion which, in turn, promotes isomerization of the olefinic bond and the formation of multiple isomers of lower linearity, as shown by their branch ratios above 0.20, as compared to a ratio of 0.19 or lower for HVI-PAO oligomers produced with reduced chromium catalysts. Olefins suitable for use as starting material in the preparation of olefinic HVI-PAO oligomers useful as starting material in the present invention include those olefins containing from 2 to about 20 carbon atoms such as ethylene, propylene, 1-butene, 1-pentene, 1-hexene, 1-octene, 1-decene, 1-dodecene and 1-tetradecene and branched chain isomers such as 4-methyl-1-pentene. Also suitable for use are olefin-containing refinery feedstocks or effluents. However, the olefins used in this invention are preferably alpha olefinic as for example 1-hexene to 1-hexadecene and more preferably 1-octene to 1-tetradecene, or mixtures of such olefins.

In the oligomerization process, the olefin feed is contacted with the oligomerization catalyst to produce the desired oligomer product. In the preparation of the liquid hydrocarbons suitable as lubricant basestocks an alpha-olefin feedstock comprising olefins of 6 to 20 carbon atoms, or mixtures of such olefins, is contacted with the oligomerization catalyst under oligomerization conditions, at a reaction temperature between 90° to 250° C. dependent upon the desired product viscosity. The higher viscosity products are made at oligomerization temperatures from about −20° to about +90° C., with the exact temperature selected being dependent upon the viscosity desired in the product. Thus, in general, the oligomerization temperature may be from about −20° to about 250° C., depending upon the characteristics, especially the viscosity, desired for the product.

In each case, the catalyst comprises a reduced metal oxide on a porous, solid support. The oxide is derived from a metal of Group VIB, preferably chromium, as the catalytic component on a porous support. The catalyst may be activated by treatment including oxidation at a temperature of 200° C. to 900° C. in the presence of an oxidizing gas and then by treatment with a reducing agent at a temperature and for a time sufficient to reduce the metal to a lower valence state. The catalyst most preferred is a lower valence Group VIB metal oxide on a porous inert support. Preferred supports include silica, alumina, titania, silica alumina, magnesia and the like. The support material binds the metal oxide catalyst. Those porous substrates having a pore opening of at least 40 Å are preferred.

The support material usually has high surface area and large pore volumes with average pore size of 40 to about 350 Å. The high surface area are beneficial for supporting large amount of highly dispersive, active chromium metal centers and to give maximum efficiency of metal usage, resulting in very high activity catalyst. The support should have large average pore openings of at least 40 Å, with an average pore opening of 60 to 300 Å preferred. This large pore opening will not impose any diffusional restriction of the reactant and product to and away from the active catalytic metal centers, thus further optimizing the catalyst productivity. Also, for this catalyst to be used in fixed bed or slurry reactor and to be recycled and regenerated many times, a silica support with good physical strength is preferred to prevent catalyst particle attrition or disintegration during handling or reaction.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200° to 900° C. by air or other oxygen-containing gas. Thereafter the catalyst is reduced by any of several various and well known reducing agents such as, for example, CO, H$_2$, NH$_3$, H$_2$S, CS$_2$, CH$_3$SCH$_3$, CH$_3$SSCH$_3$, metal alkyl containing compounds such as R$_3$Al, R$_3$B, R$_2$Mg, RLi, R$_2$Zn, where R is alkyl, alkoxy, aryl and the like. Preferred are CO or H$_2$ or metal alkyl containing compounds. Alternatively, the Group VIB metal may be applied to the substrate in reduced form, such as CrII compounds. The resultant catalyst is very active for oligomerizing olefins at a temperature range from below room temperature to about 250° C. at a pressure of 0.1 atmosphere to 5000 psi. Contact time of both the olefin and the catalyst can vary from one second to 24 hours. The catalyst can be used in a batch type reactor or in a fixed bed, continuous-flow reactor.

The support material may usually be added to a solution of the metal compounds, e.g., acetates or nitrates, etc., and the mixture is then mixed and dried at room temperature. The dry solid gel is purged with air at successively higher temperatures to about 600° for a period of about 16 to 20 hours. After this, the catalyst is cooled down under an inert atmosphere to a temperature of about 250° to 4500° C. and a stream of reducing agent such as CO or H$_2$ is contacted therewith for a period to reduce the catalyst as indicated by a distinct color change from bright orange to bluish green. Typically, the catalyst is treated with an amount of CO equivalent to a two-fold stoichiometric excess to reduce the catalyst to a lower valence CrII state. Finally the catalyst is cooled down to room temperature and is ready for use.

Further descriptions of the catalyst, its preparation and its use in the production of the HVI-PAO oligomers are given in U.S. Pat. Nos. 4,482,064 and 4,482,073 as well as in applications Ser. Nos. 07/345,606, filed May 1, 1989, now U.S. Pat. No. 5,012,020, Ser. No. 07/562,179, filed Aug. 3, 1990, Ser. No. 07/629,946, filed Dec. 19, 1990, Ser. No. 07/515/030 filed Apr. 26, 1990, now U.S. Pat. No. 5,019,670, Ser. No. 07/344,935, filed Apr. 28, 1989.

The product oligomers have atactic molecular structure of mostly uniform head-to-tail connections with some head-to-head type connections in the structure. These low branch ratio oligomers have high viscosity indices at least about 15 to 20 units and typically 30–40 units higher than equivalent viscosity prior art oligomers, which regularly have higher branch ratios and correspondingly lower viscosity indices in the lubricant products. These low branch ratios are also correlated with the pour points of the lubricant products.

The branch ratios are defined as the ratios of CH$_3$ groups to CH$_2$ groups in the oligomers are calculated from the weight fractions of methyl groups obtained by infrared methods, published in *Analytical Chemistry*. Vol. 25, No. 10, p. 1466 (1953).

$$\text{Branch ratio} = \frac{\text{wt. fraction of methyl group}}{1 - (\text{wt fraction of methyl group})}$$

In general, the HVI-PAO oligomers have the following regular head-to-tail structure where n is preferably 0 to 17, terminating in olefinic unsaturation:

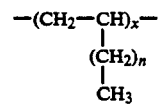

with some head-to-head connections. The as-synthesized HVI-PAO molecular structure generally has one double bond unsaturation.

The HVI-PAO process also produces a different dimer compared to the dimer produced by 1-alkene oligomerization with commercial types of catalyst such as BF$_3$ or AlCl$_3$. Typically, it has been found that a significant proportion of unhydrogenated dimerized 1-alkene has a vinylidenyl structure as follows:

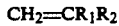

where $R_1$ and $R_2$ are alkyl groups representing the residue from the head-to-tail addition of 1-alkene molecules. For example, 1-decene HVI-PAO dimer, which participates in the post-oligomerization reaction, has been found to contain only three major components, as determined by GC. Based on $C^{13}$ NMR analysis, the unhydrogenated components were found to be 8-eicosene, 9-eicosene, 2-octyldodecene and 9-methyl-8 or 9-methyl-9-nonadecene.

The liquid lubricant compositions produced by the oligomerization process at relatively high oligomerization temperatures e.g. between 90° and 250° C., comprise $C_{30}$–$C_{1300}$ hydrocarbons, with branch ratios of less than 0.19, weight average molecular weights between 300 and 45,000, number average molecular weights between 300 and 18,000. The molecular weight distribution of these oligomers is between 1 and 5 and the pour point of the liquid lubricants is below −15° C.

The HVI-PAO oligomers, in the broadest terms, have a weight average molecular weight between 280 and 450,000 and number average molecular weight between 280 and 180,000. Measured in carbon numbers, molecular weights range from $C_{20}$ to $C_{13000}$ and viscosity up to 7500 cs at 100° C., with a preferred range of $C_{30}$ to $C_{1000}$ and a viscosity of up to 1000 cS at 100° C. for lube base stock material. Molecular weight distributions (MWD), defined as the ratio of weight average molecular to number average molecular weight, range from 1.00 to 5, with a preferred range of 1.01 to 3 and a more preferred MWD of about 1.05 to 2.5. The viscosities of the olefinic HVI-PAO oligomers used as alkylating agents in the present process will typically range from 1.5 cS to 7500 cS (measured at 100° C.).

Usually, the lubricant range oligomers are produced by varying the oligomerization temperature to yield lubricant viscosity range oligomers having weight average molecular weight between 420 and 45,000 and number average molecular weight between 420 and 18,000. Measured in carbon numbers, molecular weights range from $C_{30}$ to $C_{1300}$ and a viscosity up to 750 cs at 100° C., with a preferred range of $C_{30}$ to $C_{1000}$ and a viscosity of up to 500 cS at 100° C. Molecular weight distributions (MWD), defined as the ratio of weight average molecular to number average molecular weight, range from 1.00 to 5, with a preferred range of 1.01 to 3 and a more preferred MWD of about 1.05 to 2.5. Compared to conventional PAO derived from $BF_3$- or $AlCl_3$-catalyzed polymerization of 1-alkene, HVI-PAO has been found to have a higher proportion of higher molecular weight polymer molecules in the product.

The viscosities of the lubricant HVI-PAO oligomers measured at 100° C. range from 3 cS to 5000 cS. The viscosity index for the liquid polyalpha-olefins is approximately described by the following equation:

$$VI = 156.8 + 4.94 \times (V_{100° C.})^{0.5},$$

where $V_{100° C.}$ is the kinematic viscosity in centistokes measured at 100° C.

The higher viscosity oligomers produced at oligomerization temperatures below about 90 C. comprise hydrocarbons which have a branch ratio below 0.19 and a viscosity at 100° C. which is typically from 100 to 20,000 cS. The hydrocarbons typically have weight average molecular weights from 15,000 to 200,000 and number average molecular weights from 5,000 to 50,000 with a molecular weight distribution from about 1 to about 5. The viscosity index of the liquid compositions of this type is at least 130 and usually higher, for example, above 180 or even 200 or higher. The high viscosity materials are characterized by high shear stability, being stable under high temperature, high shear rate conditions, notably at 150° C. and a shear rate of one million ($10^6$) reciprocal seconds. Reference is made to Ser. No. 07/345,606 for a more detailed description of these oligomers, their properties and uses as well of the methods by which they may be made.

As oligomerized, the HVI-PAO oligomers are mixtures of dialkyl vinylidenic and 1,2 dialkyl or trialkyl mono-olefins and the lower molecular weight unsaturated oligomers are usually hydrogenated to produce the thermally and oxidatively stable lubricants after removal of the non-lube boiling range fraction (dimer and lower) by distillation. In the present process, however, the crude oligomerization mixture i.e. the total effluent from the oligomerization process is treated with an aromatic compound in the presence of an acidic catalyst to improve the yield and stability of the product.

AROMATIC COMPONENT

In the present process, the thermal and oxidative stabilities and solvency characteristics of the oligomers are improved by adding an aromatic compound to the total oligomerization mixture containing the non-lube range dimer and unoligomerized olefin together with any other products of the initial oligomerization process, and carrying out a reaction in the presence of the acidic catalyst.

The aromatic compound which is used in this step of the process is usually a monocyclic or bicyclic aromatic compound. Aromatic compounds which may be used include substituted and unsubstituted benzene compounds such as benzene itself, toluene, the isomeric xylenes, ethylbenzene, cumene and bicyclic polycyclic aromatic compounds, particularly naphthalene, anthracene and phenanthracene. Typical useful aromatic hydrocarbons for the present invention include benzene, toluene, o,m,p-xylene, hemimellitene, pseudocumene, ethylbenzene, n-propylbenzene, cumene, n-butylbenzene, isobutylbenzene, sec-butylbenzene, tert-butylbenzene, p-cymene, biphenyl, diphenylmethane, triphenyl methane, 1,2-diphenylethane and similarly alkyl substituted naphthalenes and anthracenes; also phenol, catechol, acylphenol such as acetylphenol, carbonate esters such as phenyl methyl or ethyl carbonate and diphenyl carbonate, alkylphenol such as anisole, chloro and bromobenzene, aniline, acyl aniline such as acetanilide, methyl and ethylbenzoate, thiophenol and acylated thiophenol, nitrobenzene, diphenylether, diphenylsulfide and similarly substituted naphthalenes and anthracenes, in particular naphthols such as mono and dihydroxy naphthalene.

CATALYST

The post-oligomerization process is carried out in the presence of an acidic catalyst. The catalyst may be a heterogeneous catalyst which can be readily separated from the reaction mixture by filtration or other mechanical means or, alternatively, homogeneous catalysts may be used. The catalysts are characterized by the possession of acidic functionality i.e. are Lewis acids or Brønsted acids. Suitable homogeneous acid catalysts include acids such as $BF_3$ or $AlCl_3$ and their complexes, for example, complexes of $BF_3$ with water, alcohols or esters, as well as other homogeneous acids such as trifluoromethanesulfonic acid (triflic acid). Supported homogeneous catalysts such as $AlCl_3$ or $BF_3$ on graphite, or $AlCl_3$ on silica, alumina may be used. Solid, heterogeneous acid catalysts which may be used include acidic clays including surface-modified clays, porous amorphous solids such as the acidic metal oxides, e.g. alumina, silica and silica-alumina and crystalline solids, especially the zeolites. Zeolites which may be used include the large pore size zeolites such as zeolites X, Y (especially USY), mordenite and zeolite beta, and the intermediate pore size zeolites such as ZSM-5, ZSM-11 and ZSM-12 possessing a Constraint Index from 2 to 10. Constraint Index and the method for measuring it are defined in U.S. Pat. No. 4,016,218. Other solid materials such as the acidic layered materials are also suitable catalysts.

A preferred catalytic material for use in the present process is the acidic zeolite material MCM-22, which is described in U.S. Pat. No. 4,954,325, to which reference is made for a description of this material, its properties and its preparation.

POST-OLIGOMERIZATION REACTION

The molar ratio of the aromatic compound to the unsaturated double bonds in the crude mixture from the oligomerization step can typically be from about 0.1:1 to about 50:1, and is usually in the range from about 0.5:1 to about 5:1. The preferred amount of aromatic relative to the crude mixture is from about 2 to 50 weight percent of the crude oligomerization mixture.

The reaction can be carried out as a batch-type process or in a semi-continuous or continuous operation suitably utilizing a fixed bed catalyst system. The reaction of the aromatic compound with the oligomerization mixture is suitably effected at a temperature of between about ambient and about 300° C., and preferably between about 50° C. and about 250° C. The reaction generally takes place at sufficient pressure to maintain the reactants in the liquid phase, normally at pressures of from about 0.2 to about 250 atmospheres (gauge) and preferably at not more than about 5 atmospheres gauge. Reaction is suitably accomplished utilizing a feed weight hourly space velocity (WHSV) of between about 0.1 $hr^{-1}$ and about 10 $hr^{-1}$ and preferably from 0.5 $hr^{-1}$ to about 2 $hr^{-1}$ in a fixed bed process using a solid catalyst (WHSV based upon the total weight of active catalyst and binder, if present).

By varying the ratio of the aromatic compound relative to the olefin oliogmer, the viscosity and VI of the reaction product may be varied. As a general rule, the greater the amount of the aromatic relative to the oligomer, the more stable will be the product although at some cost in VI. The amount of dimer and unreacted-/isomerized starting material in the initial oligomerization mixture will also affect the characterisitics of the product, although a degradation of the desirable viscometric properties is not usually associated with the presence of significant quantities of the dimer and unreacted/isomerized starting material in the reaction mixture. The incorporation of the dimer and the unreacted/isomerized olefin into the product does, however, tend to increase the yield of the process, so that olefin utilization is improved at the same time as the properties of the product.

The reaction is carried out using the unhydrogenated oligomerization mixture containing the oligomer, dimer and olefin and during the course of the reaction, residual unsaturation in the oligomer is mostly eliminated, so that the final product is almost completely saturated although some residual unsaturation may remain, indicative of incomplete reaction. This residual unsaturation may be removed by hydrotreating the reaction product so that the bromine number of the product is reduced and, in certain instances, the color of the product improved, especially when aluminum trichloride is used as the catalyst. Mild hydrotreating conditions are suitable, for example, temperatures below 250° C. with a mild catalyst such as nickel on kieselguhr at a low catalyst loading. If hydrofinishing is excessive, the aromatic components in the lube product may become saturated and although the finished product may be water-white, the thermal stability may not be as high as in the mildly hydrotreated product.

The improvement in the thermal stability of the product may be attributed to the key reaction between the olefin oligomer and the aromatic compound but, in addition, isomerization of the skeletal structure of the oligomer also occurs. The extent to which skeletal isomerization of the oligomer takes place during the reaction with the aromatic depends on the conditions employed and the catalyst. At reaction temperatures below about 200° C., the Lewis acid catalysts such as aluminum trichloride and boron trifluoride tend to promote isomerization, with the extent of isomerization increasing with increasing temperature while at temperatures above about 200° C. the solid catalysts such as the zeolites will also promote isomerization. Isomerization of the HVI-PAO oligomer may occur either before or after the attachment to the aromatic compound.

PRODUCTS

The aromatic-containing compounds which are produced by the process are believed to be reaction products derived from the reaction of the oligomer with aromatic compounds as well as by reaction of the oligomer with the dimer and with the isomerized olefin and possibly, the original olefin.

The products of the process are useful as lubricant basestock and as additives for both mineral and synthetic lubricants. The higher molecular weight products are especially useful as multipurpose lubricant additives since they have excellent VI improvement properties which may be combined with other valuable additive characteristics. The introduction of the aromatic moiety into the HVI-PAO increases thermal stability, increases solubilizing power of the product and may add other properties useful in additives such as antiwear properties and VI enhancement. Therefore, as additives, their usefulness is compounded to incorporate in a single additive product the capability to improve a lube basestock thermal stability, VI, solvency and seal swelling power as well as improving antiwear characteristics. They possess the further advantage of great flexibility in the range of viscosity in which they can be prepared so that their additive properties can be used in a viscosity compatible with the viscosity formulation of the lube basestock.

EXAMPLE 1

The crude HVI-PAO starting material used for the following examples were synthesized according to U.S. Pat. No. 4,827,064 or U.S. Pat. No. 4,827,073 at varying temperatures to produce products of different viscosities in the range of 6 to 12 cS (100° C.) The crude HVI-PAO contained unreacted 1-decene, isomerized decenes, $C_{20}$ olefins (dimer) and trimer and higher olefins in the lube range. The lubricant fraction was then hydrogenated to remove any unsaturation for comparison purposes.

EXAMPLES 2-14

Synthesis of modified HVI-PAO and the product properties

The crude HVI-PAO produced in Example 1, proper amount of aromatic compound and catalyst were mixed in a flask or an autoclave and then heated to reaction temperature for certain period of time. The lubricant fraction was then isolated after removal of the catalysts by either filtration or by washing with dilute acid and base followed by vacuum distillation to remove material boiling below $\sim 120°$ C./0.1 mm Hg. The lubricant product can be further hydrofinished under mild conditions (Ni/kieselguhr) to remove any residual unsaturation or to improve product color. The thermal stability of the product was tested by heating a degassed sample of 5 to 10 grams at 280° C. or 300° C. under static nitrogen for 24 hours. At high temperature, the lubricant molecules break down into smaller molecules with lower viscosities. The thermal stability was expressed in percentage viscosity change compared to the initial viscosity. Lubricant products with a lower percentage viscosity loss are considered more thermally stable.

Tables 1 to 3 summarize the compositions of starting crude HVI-PAO and the reaction conditions for the modified HVI-PAO synthesis including types of aromatic compounds and catalysts used and the properties of modified HVI-PAOs. Examples 2 to 7 of Table 1 show the lubricant yields of HVI-PAO in the starting crude mixture are 59% to 74%. However, after reaction with aromatic compounds, such as naphthalene, toluene, and xylenes, over acid catalysts, such as acid clay Filtrol 22 (trade mark) or amorphous silica alumina, the lubricant yields increased to 81% to 92%. Furthermore, the lubricant products had much better thermal stability than the HVI-PAOs of similar viscosities. For instance, in Example 2, the modified HVI-PAO showed no viscosity loss at all when heated to 280° and 300° C. for 24 hours instead a slight viscosity increase of 5% and 2% was observed. In comparison, a 15 cS HVI-PAO would lose 25 to 32% viscosity under the same condition. Examples 8 to 11 in Table 2 demonstrated that the lubricant yields of medium viscosity products 40-60 cS increased from 88-90% to 98%. The product thermal stabilities were also dramatically improved. An unmodified HVI-PAO of 40-50 cS generally lose 50-60% of its viscosity at 300° C. for 24 hours. Under the same conditions, the modified HVI-PAO lose only up to 8% of its initial viscosity. These Examples also demonstrated the use of methylnaphthalene as the aromatic component and acidic catalysts such as $AlCl_3$, solid $AlCl_3$ on graphite or MCM-22 in the preparations of modified HVI-PAOs.

Examples 12 to 14 in Table 3 demonstrated that high viscosity modified HVI-PAO can be produced in good yields with improved thermal stability. After thermal treatment at 300° C. for 24 hours, the products lose only 8 to 34% of their starting viscosities compared to 65-75% for the comparable HVI-PAOs.

TABLE 1

| Example | 2 | 3 | 4 | 5 | 6 | 7 |
|---|---|---|---|---|---|---|
| Compn. of starting crude HVI-PAO | | | | | | |
| $C_{10}$ | 27.7 | 15.1 | 15.1 | 12.4 | 12.4 | 12.4 |
| $C_{20}$ | 12.9 | 17.2 | 17.2 | 13.5 | 13.5 | 13.5 |
| NVI-PAO ($C_{30}+$) | 59.4 | 66.7 | 66.7 | 74.1 | 74.1 | 74.1 |
| Lube properties of HVI-PAO in crude mixture | | | | | | |
| V, 100° C., cS | 6.93 | 10.34 | 10.34 | 11.92 | 11.92 | 11.92 |
| VI | 157 | 158 | 158 | 169 | 169 | 169 |
| Bromine No. | — | 16 | 16 | — | — | — |
| Reaction conditions for modified HVI-PAO synthesis | | | | | | |
| Aromatic | Naphth. | Naphth. | Naphth. | Tol. | Xyl. | Toluene |
| Catalyst | Clay | $SiO_2/Al_2O_3$ | Clay | Clay | Clay | Triflic Acid |
| Rxn Temp., °C. | 150 | 180 | 180 | 150 | 150 | 100 |
| Rxn Time, hours | 16 | 16 | 16 | 16 | 72 | 72 |
| Wt % aromatic | 30 | 25 | 25 | 18 | 20 | 18 |
| Hydro-finish | no | no | no | yes | yes | yes |
| Product Composition. wt % | | | | | | |
| $C_{10}$ | 0 | 0 | 0.3 | 2.1 | 0 | 0.5 |
| $C_{10}$-$C_{20}$ | 19.3 | 7.6 | 9.0 | 6.5 | 10 | 7.7 |
| Lube | 80.7 | 92.4 | 90.7 | 91.6 | 90 | 91.8 |
| Lube product properties | | | | | | |
| V, 100° C., cS | 14.81 | 14.13 | 16.91 | 15.12 | 16.02 | 17.66 |
| VI | 102 | 124 | 122 | 153 | 138 | 144 |
| Bromine No. | 3.2 | 2.5 | 1.11 | 1.0 | 3.1 | 1.2 |
| Pour Point, °C. | — | — | — | −45 | <−36 | — |
| Thermal Stability Test, in % viscosity change | | | | | | |
| 280° C., 24 h | +5 | +4 | +3 | −9 | −19 | −22 |
| 300° C., 24 h | +2 | +2 | +1 | −15 | −30 | −32 |

Notes:
Naph. = Naphthalene,
Tol. = Toluene,
Xyl. = Xylene
Clay = Filtrol 22 (trade mark), an acidic clay catalyst of Harshaw Catalyst Company.

TABLE 2

| Example | 8 | 9 | 10 | 11 |
|---|---|---|---|---|
| Compn. of starting crude HVI-PAO | | | | |
| $C_{10}$ | 5.5 | 5.6 | 4.8 | 7.0 |
| $C_{20}$ | 6.7 | 6.3 | 3.6 | 2.0 |
| HVI-PAO ($C_{30}+$) | 87.7 | 88.1 | 91.6 | 91.0 |
| Lube properties of HVI-PAO in crude mixture | | | | |
| V, 100° C., cS | 19 | 29.7 | 26 | 39 |
| VI | — | 178 | — | 180 |
| Bromine no. | — | 7.2 | — | — |
| Reaction condns. for modified HVI-PAO synthesis | | | | |
| Aromatic | Naph. | Naph. | Naph. | Me-Naph. |
| Catalyst | Clay | $AlCl_3$ | $AlCl_3$/C | MCM-22 |
| Temp., °C. | 200 | 100 | 225 | 250 |
| Time, hours | 48 | 4 | 24 | 18 |
| Wt % aromatic | 7.5 | 5.9 | 10 | 5 |
| Hydro-finish | no | yes | yes | no |
| Product Composition, wt % | | | | |
| $C_{10}$ | 1.5 | 0.4 | 2.4 | — |
| $C_{10}$–$C_{20}$ | 6.1 | 1.2 | 4.2 | — |
| Lube | 92.4 | 98.4 | 93.4 | 87.4 |
| Lube product properties | | | | |
| V, 100° C., cS | 36.34 | 66.4 | 50.99 | 53 |
| VI | 146 | 158 | 157 | 167 |
| Bromine No. | 1.2 | 1.3 | 1.3 | 3.2 |
| Pour Point, °C. | −44 | — | — | — |
| Thermal stability, pct. viscosity change | | | | |
| 280° C., 24 h | +4.3 | — | +5.0 | — |
| 300° C., 24 h | −4.4 | −4.1 | +1.2 | −8 |

Notes:
Naph. = Naphthalene,
Tol. = Toluene,
Xyl. = Xylene,
Me-Naph = Methylnaphthalene
Clay = Filtrol 22 (trade mark), an acidic clay catalyst of Harshaw Catalyst Company.
$AlCl_3$/C = 35–40% Aluminum chloride on graphite available from Alpha Products (P.O. Box 8247, Ward Hill, MA 01835).

TABLE 3

| Example | 12 | 13 | 14 |
|---|---|---|---|
| Compn. of starting crude HVI-PAO | | | |
| $C_{10}$ | 7.2 | 5 | 5 |
| $C_{20}$ | 2.6 | 5 | 5 |
| HVI-PAO ($C_{30}+$) | 90.2 | 90 | 90 |
| Lube properties of HVI-PAO in crude mixture | | | |
| V, 100C, cS | 87.0 | 90 | 90 |
| VI | 203 | 194 | 194 |
| Bromine no. | 3.9 | 5.1 | 5.1 |
| Reaction condtns for modified HVI-PAO synthesis | | | |
| Aromatic | Naph. | Me-Naph. | Me-Naph |
| Catalyst | $AlCl_3$ | MCM-22 | USY |
| Temp., °C. | 100 | 250 | 210 |
| Time, hours | 4 | 18 | 17 |
| Wt % aromatic | 6.4 | 5 | 5 |
| Hydro-finish | yes | no | no |
| Product Composition, wt % | | | |
| $C_{10}$ | 0.5 | — | — |
| $C_{10}$–$C_{20}$ | 2.8 | — | — |
| Lube | 96.4 | 90.0 | — |
| Lube product properties | | | |
| V, 100C, cS | 131.5 | 103 | 87 |
| VI | 179 | 187 | 198 |
| Bromine No. | 0.9 | 3.5 | 4.8 |
| Thermal stability, pct. viscosity change | | | |
| 280° C., 24 h | — | — | — |
| 300° C., 24 h | −7.9 | −18 | −34 |

Notes:
Naph. = Naphthalene,
Tol. = Toluene,
Xyl. = Xylene,
Me-Naph = Methylnaphthalene

We claim:

1. A process for the preparation of an olefin oligomer derivative of improved stability in improved yield, which comprises:

oligomerizing a 1-olefin in the presence of a reduced metal oxide catalyst to produce an oligomerization product comprising an olefinic hydrocarbon oligomer having a branch ratio less than 0.19 and olefinic dimer, reacting the oligomerization product mixture with an aromatic compound in the presence of an acidic catalyst to produce an oligomer derivative of improved stability in improved yield.

2. A process according to claim 1 in which the oligomerization product comprises the product of the oligomerization under oligomerization conditions of a $C_2$–$C_{20}$ 1-alkene in contact with supported reduced metal oxide oligomerization catalyst comprising a lower valence state form of at least Group VIB metal.

3. A process according to claim 2 in which the supported reduced metal oxide catalyst comprises reduced chromium oxide on silica support.

4. A process according to claim 2 in which the oligomerization conditions comprise a temperature between 90° and 250° C.

5. A process according to claim 1 in which the olefin oligomer comprises a $C_{30}$ to $C_{13000}$ liquid lubricant oligomer having a weight average molecular weight between 280 and 450,000 and number average molecular weight between 280 and 180,000.

6. A process according to claim 5 in which the molecular weight distribution of the olefin oligomer is from 1.00 to 5.

7. A process according to claim 5 in which the olefin oligomer has a viscosity of 1.5 to 300° cS at 100° C.

8. A process according to claim 5 in which the olefin oligomer has viscosity of 3 to 10 cS at 100° C.

9. A process according to claim 1 in which the olefin is a $C_8$ to $C_{14}$ 1-olefin or mixture of olefins.

10. A process according to claim 1 in which the olefin is 1-decene.

11. A process according to claim 1 in which the reaction with the aromatic compound is carried out at a temperature of up to about 300° C.

12. A process according to claim 11 in which the reaction with the aromatic compound is carried out at a temperature from about 50° to about 250° C.

13. A process according to claim 1 in which the aromatic compound comprises a monocyclic aromatic hydrocarbon.

14. A process according to claim 13 in which the aromatic hydrocarbon comprises benzene or an alkylbenzene.

15. A process according to claim 1 in which the aromatic compound comprises a bicyclic aromatic hydrocarbon.

16. A process according to claim 15 in which the aromatic hydrocarbon comprises naphthalene or a substituted naphthalene.

17. A process according to claim 1 in which the molar ratio of the aromatic compound to the unsaturated double bonds in the crude mixture from the oligomerization step is from about 0.1:1 to about 50:1.

18. A process according to claim 17 in which the molar ratio of the aromatic compound to the unsaturated double bonds in the crude mixture from the oligomerization step is from about 0.5:1 to about 5:1.

19. A process according to claim 1 in which the amount of aromatic compound relative to the oligomerization mixture is from about 2 to 50 weight percent of the oligomerization mixture.

* * * * *